(12) United States Patent
Horiuchi

(10) Patent No.: US 6,463,115 B1
(45) Date of Patent: Oct. 8, 2002

(54) PROJECTION DATA CORRECTION METHOD AND APPARATUS, AND RADIATION TOMOGRAPHIC IMAGING METHOD AND APPARATUS

(75) Inventor: Tetsuya Horiuchi, Tokyo (JP)

(73) Assignee: GE Yokogawa Medical Systems, Limited, Tokyo (JP)

( * ) Notice: Subject to any disclaimer, the term of this patent is extended or adjusted under 35 U.S.C. 154(b) by 202 days.

(21) Appl. No.: 09/636,288

(22) Filed: Aug. 10, 2000

(30) Foreign Application Priority Data

Aug. 10, 1999 (JP) .......................................... 11-226295
Jun. 2, 2000 (JP) ...................................... 2000-165334

(51) Int. Cl.$^7$ ................................................. A61B 6/03
(52) U.S. Cl. ........................................... 378/4; 378/901
(58) Field of Search ............................... 378/4, 62, 901

(56) References Cited

U.S. PATENT DOCUMENTS 6,373,919 B1 * 4/2002 Horiuchi ........................ 378/4

* cited by examiner

Primary Examiner—David V. Bruce
(74) Attorney, Agent, or Firm—Moonray Kojima

(57) ABSTRACT

In order to provide a projection data correction method and apparatus that prevents artifact generation in the direction which provides a low count of penetrating radiation, and a radiation tomographic imaging method employing such a projection data correction method and a radiation tomographic imaging apparatus comprising the projection data correction apparatus, projection data $Proj\_ij$ is individually corrected by a weighted addition (604, 606, 608) with an average value (602) containing the proximate data. The weight $SG_{ij}$ of the projection data is decreased as the count of the penetrating radiation from which the projection data is derived becomes smaller.

18 Claims, 8 Drawing Sheets

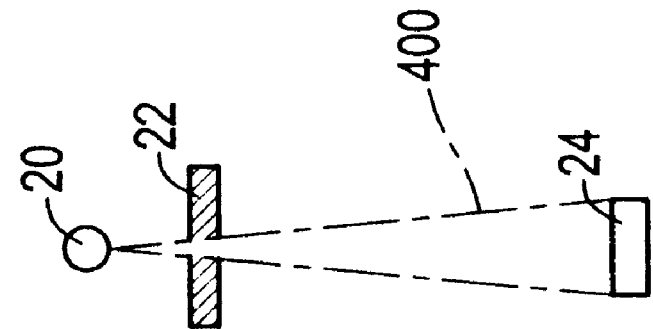
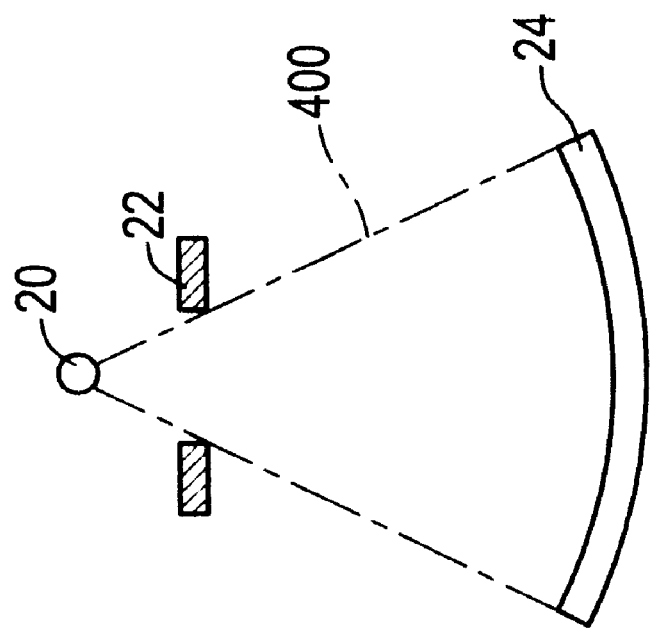

PROJECTION DATA CORRECTION METHOD AND APPARATUS, AND RADIATION TOMOGRAPHIC IMAGING METHOD AND APPARATUS

BACKGROUND OF THE INVENTION

The present invention relates to a projection data correction method and apparatus and a radiation tomographic imaging method and apparatus, and more particularly to a method and apparatus for individually correcting data constituting a projection of an object to be imaged by. penetrating radiation, and a radiation tomographic imaging method employing such a projection data correction method and a radiation tomographic imaging apparatus, comprising the projection data correction apparatus.

In a radiation tomographic imaging apparatus employing an X-ray, i.e., an X-ray. CT (computerizes tomography) apparatus, an X-ray beam having a width containing a range to be imaged and having a thickness in a direction orthogonal to the width is emitted from an X-ray emitting apparatus. The thickness of the X-ray beam can be changed by regulating the openness of an X-ray passing aperture of a collimator, and the slice thickness for imaging is thus adjusted.

An X-ray detecting apparatus comprises a multi-channel X-ray detector to detect an X-ray, and the detector has a multiplicity (e.g., of the order of 1,000) of X-ray detector elements arranged in an array in the direction of the X-ray width.

The X-ray emitting/detecting apparatus is rotated (or scans) around an object to be imaged to generate X-ray projection data of the object in a plurality of view directions around the object, and a tomographic image is produced (or reconstructed) by a computer based on the projection data.

The SNR (signal-to-noise ratio) of the projection data is varied with the 'count' of the penetrating X-ray, and a smaller count gives a lower SNR, if the object to be imaged provides significantly different counts, i.e., significantly different SNR's of the projection data, depending on the view direction, the reconstructed image suffers from false linear images, or so-called streaking artifacts, due to the effect of a noise pattern in the direction which provides a poor SNR.

Thus, when the thorax or abdomen is imaged with both the arms put on the sides of the body, for example, the streaking artifacts inevitably appear in the direction which connects the arms, leading to a problem that an image having a good quality cannot be obtained.

SUMMARY OF THE INVENTION

The present invention is directed to solving the aforementioned problem, and the object of the invention is to provide a projection data -correction method and apparatus that prevents artifact generation in the direction which provides a low count of penetrating radiation, and a radiation tomographic imaging method employing such a projection data correction method and a radiation tomographic imaging apparatus comprising the projection data correction apparatus.

(1) In accordance with a first aspect of the invention to solve the aforementioned problem, there is provided a projection data correction method comprising the steps of: individually calculating an average value of data and its proximate data, the data constituting a projection of an object to be imaged by penetrating radiation; calculating a first product by multiplying the data by a first weighting factor that corresponds to a count of the penetrating radiation from which the data is derived; calculating a second product by multiplying the average value by a second weighting factor that is a complement of the first weighting factor with respect to one; and adding the first and second products.

(2) In accordance with a second aspect of the invention to solve the aforementioned problem, there is provided a projection data correction apparatus comprising: average value. calculating means for individually calculating an average value of data and its proximate data, said data constituting a projection of an object to be imaged by penetrating radiation; first product calculating means for calculating a first product by multiplying said data by a first weighting factor that corresponds to a count of the penetrating radiation from which said data is derived; second product calculating means for calculating a second product by multiplying said average value by a second weighting factor that is a complement of said first weighting factor with respect to one; and adder means for adding said first and second products.

(3) In accordance with a third aspect of the invention to solve the aforementioned problem, there is provided a radiation tomographic imaging apparatus comprising: radiation emitting/detecting means for. emitting radiation toward an object to be imaged in a plurality of view directions and detecting penetrating radiation, and image producing means for producing an image using a projection based on signals detected by said radiation emitting/detecting means, wherein said image producing means comprises: average value calculating means for individually calculating an average value of data and its proximate data, said data constituting said projection; first product calculating means for calculating a first product by multiplying said data by a first weighting factor that corresponds to a count of the penetrating radiation from which said data is derived; second product calculating means for calculating a second product by multiplying said average value by a second weighting factor that is a complement of said first weighting factor with respect to one; adder means for adding said first and second products; and image reconstruction means for reconstructing an image using a projection comprised of data resulted from said addition.

(4) In accordance with a fourth aspect of the invention to solve the aforementioned problem, there is provided the radiation tomographic imaging apparatus as described in (3), wherein an X-ray is employed as the radiation.

(5) In accordance with a fifth aspect of the invention to solve the aforementioned problem, there is provided the above-described projection data correction method, wherein the first weighting factor decreases as the corresponding count becomes smaller.

(6) In accordance with a sixth aspect of the invention to solve the aforementioned problem, there is provided the above-described projection data correction method, comprising the step of employing data obtained by a scout scan or data of a view of an axial scan to determine a rate at which the first weighting factor decreases as the corresponding count becomes smaller.

(7) In accordance with a seventh aspect of the invention to solve the aforementioned problem, there is provided the above-described projection data correction apparatus, comprising first weighting factor determining means for determining the first weighting factor so that the first weighting factor decreases as the corresponding count becomes smaller.

(8) In accordance with an eighth aspect of the invention to solve the -aforementioned problem, there is provided the above-described projection data correction apparatus, wherein the first weighting factor determining means employs data obtained by a scout scan or data of a view of an axial scan to determine a rate at which the first weighting factor is decreased as the corresponding count becomes smaller, (9) In accordance with a ninth aspect of the invention, to solve the aforementioned problem, there is provided the above-described radiation tomographic imaging apparatus, comprising first weighting factor determining means for determining the first weighting factor so that the first weighting factor decreases as the corresponding count becomes smaller.

(10) In accordance with a tenth aspect of the invention to solve the aforementioned problem, there is provided the above-described radiation tomographic imaging apparatus, wherein the first weighting factor determining means employs data obtained by a scout scan or data of a view of an axial scan to determine a rate at which the first weighting factor is decreased as the corresponding count becomes smaller.

In any one of (1)–(10), it is preferred that the first weighting factor be given by the following equation:

First weighting factor=$1-\exp\{-C/\alpha\}$,

Insofar as artifacts are effectively prevented, wherein

C: a count of the penetrating radiation from which the data is derived, and

α: a constant determined by the area of the projection.

It is preferred that the constant a be determined employing data obtained by a scout scan or data of a start view of an axial scan, and finding a value of the constant a from the area of the projection of that data by an equation or a table.

(Effect)

According to the present invention, the projection: data is individually corrected by a weighted addition with an average value containing the proximate data. The weight of the data is made to correspond to the count of penetrating radiation from which the data is derived. Thus, data with a lower count has a smaller weight of that data and a greater weight of the average value, which can compensate for reduction in SNR.

Moreover, according to the present invention, when the weight of data is decreased and the weight of an average value is increased as the count becomes smaller, a rate at which the weight of data is decreased and a rate at which the weight of an average value is increased as the count becomes smaller are determined employing data obtained by a scout scan or data of a view of an axial scan. Thus, the correction can be relatively weakened by reducing the rate when the size of the object to be imaged is large and streaking artifacts are relatively avoided (i.e., when the difference in SNR of projection data depending on the view direction is relatively small); and the correction can be relatively strengthened by increasing the rate when the size of the object to be imaged is small and streaking artifacts relatively tend to appear (i.e., when the difference in SNR of projection data depending on the view direction is relatively large). Accordingly, a suitable correction can be made regardless of the size of the object to be imaged.

Thus, the present invention can provide a projection data correction method and apparatus that prevents artifact generation in the direction which provides a low count of penetrating radiation, and a radiation tomographic imaging apparatus comprising such a projection data correction apparatus.

Further objects and advantages of the present invention will be apparent from the following description of the preferred embodiments of the invention as illustrated in the accompanying drawings,

BRIEF DESCRIPTION OF THE DRAWINGS

FIGS. 3 and 4 are schematic diagrams showing the X-ray emitting/detecting apparatus in the apparatus shown in FIG. 1.

DETAILED DESCRIPTION OF THE INVENTION

Figure 1:
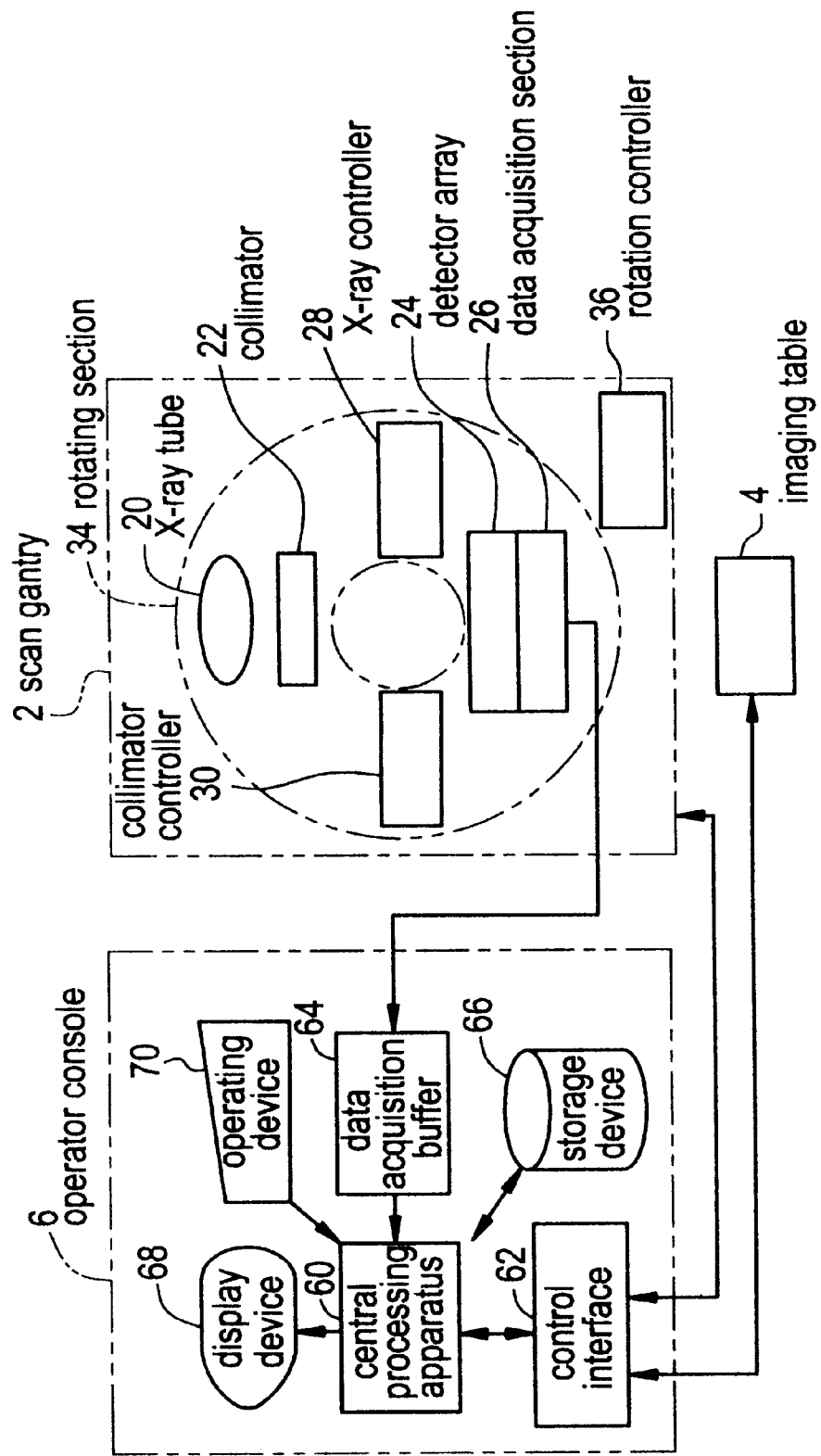
FIG. 1 is a block diagram of an apparatus in accordance with an embodiment of the present invention.

Several embodiments of the present invention will now be described in more detail with reference to the accompanying drawings. FIG. 1 shows a block diagram of an X-ray CT apparatus, which is an embodiment of the present invention. The configuration of the apparatus represents an embodiment of the apparatus in accordance with the present invention, and the operation of the apparatus represents an embodiment of the method in accordance with the present invention.

As shown in FIG. 1, the apparatus comprises a scan gantry 2, an imaging table 4 and an operator console 6. The scan gantry 2 is an embodiment of the radiation emitting/detecting means of the present invention. The scan gantry 2 has an X-ray tube 20. An X-ray (not shown) emitted from the X-ray tube 20 is formed into, for example, a fan-shaped X-ray beam, i.e., a fan beam, by a collimator 22, and cast upon a detector array 24. The detector array 24 has a plurality of X-ray detector elements arranged in an array in the direction of the fan-shaped X-ray beam spread. The configuration of the detector array 24 will be described later.

The X-ray tube 20, collimator 22 and detector array 24 together constitute an X-ray emitting/detecting apparatus, which will be described later. The detector array 24 is connected with a data acquisition section 26 for acquiring data detected by the individual X-ray detector elements in the detector array 24.

The emission of the X-ray from the X-ray tube 20 is controlled by an X-ray controller 28. The connection relationship between the X-ray tube 20 and the X-ray controller 28 is omitted in the drawing. The collimator 22 is controlled by a collimator controller 30. The connection relationship between the collimator 22 and the collimator controller 30 is omitted in the drawing.

The above-described components from the X-ray tube 20 through the collimator controller 30 are supported on a rotating section 34 of the scan gantry 2. The rotation of the rotating section 34 is controlled by a rotation controller 36. The connection relationship between the rotating section 34 and the rotation controller 36 is omitted in the drawing.

The imaging table 4 is configured to carry an object to be imaged (not shown in FIG. 1) into and out of an X-ray irradiation space in the scan gantry 2. The relationship between the object to be imaged and the X-ray irradiation space will be described later.

The operator console 6 has a central processing apparatus 60, which is comprised of, for example, a computer. The central processing apparatus 60 is connected with a control interface 62, which is in turn connected with the scan gantry 2 and the imaging table 4. The central processing apparatus 60 controls the scan gantry 2 and the imaging table 4 via the control interface 62.

The data acquisition section 26, X-ray controller 28, collimator controller 30 and rotation controller 36 in the scan gantry 2 are controlled via the control interface 62. The individual connections between these sections and the control interface 62 are omitted in the drawing.

The central processing apparatus 60 is also connected with a data acquisition buffer 64, which is in turn connected with the data acquisition section 26 in the scan gantry 2. Data acquired at the data acquisition section 26 is input to the data acquisition buffer 64, and the buffer 64 temporarily stores the input data.

The central processing apparatus 60 performs data correction for projections of a plurality of views acquired via the data acquisition buffer 64, and performs image reconstruction using the corrected projection data. The central processing apparatus 60 is an embodiment of the image producing means, and is also an embodiment of the image reconstruction means of the present invention. The image reconstruction is performed using a filtered back projection technique, for example.

The central processing apparatus 60 is also connected with a storage device 66 for storing several data, reconstructed images, programs and so forth. The central processing apparatus 60 is moreover connected with a display device 68 that displays the reconstructed image and other information output from the central processing apparatus 60, and an operating device 70 that is operated by a human operator to supply several instructions and information to the central processing apparatus 60.

Figure 2:
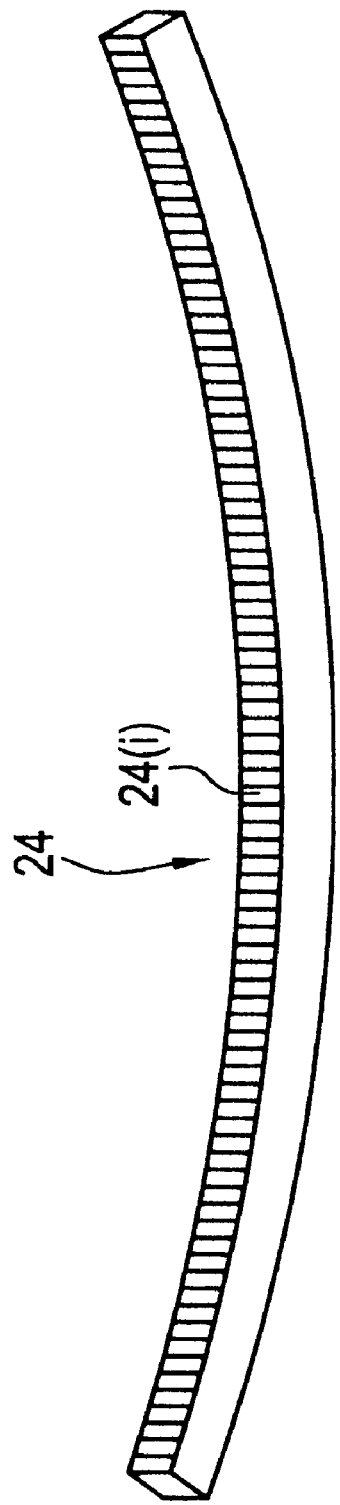
FIG. 2 is a schematic diagram showing the detector array in the apparatus shown in FIG. 1.

FIG. 2 schematically illustrates a configuration of the detector array 24. The detector array 24 is a multi-channel X-ray detector having a multiplicity of X-ray detector elements 24(i) arranged in a row. The multiplicity of the X-ray detector elements 24(i) together form an X-ray impinging surface curved into a cylindrical concave surface. Reference symbol 'i' designates a channel index and 'i'=1–1,000, for example.

Each X-ray detector element 24(i) is formed of a combination of a scintillator and a photodiode, for example. It will be easily recognized that the X-ray detector element 24(i) is not limited thereto but may be a semiconductor X-ray detector element using cadmium telluride (CdTe) or the like, or an ionization chamber X-ray detector element using xenon (Xe) gas, for example.

FIG. 3 illustrates a relationship among the X-ray tube 20, collimator 22 and detector array 24 in the X-ray emitting/detecting apparatus. FIG. 3(*a*) is a view from the front of the scan gantry 2 and (*b*)

In FIG. 3(*a*), the spread of the fan-shaped X-ray beam 400, i.e., the width of the X-ray beam 400 is illustrated. The direction of the width of the X-ray beam 400 is identical to the direction of the channel row in the detector array 24. In FIG. 3(*b*), the thickness of the X-ray beam 400 is illustrated.

Figure 4:
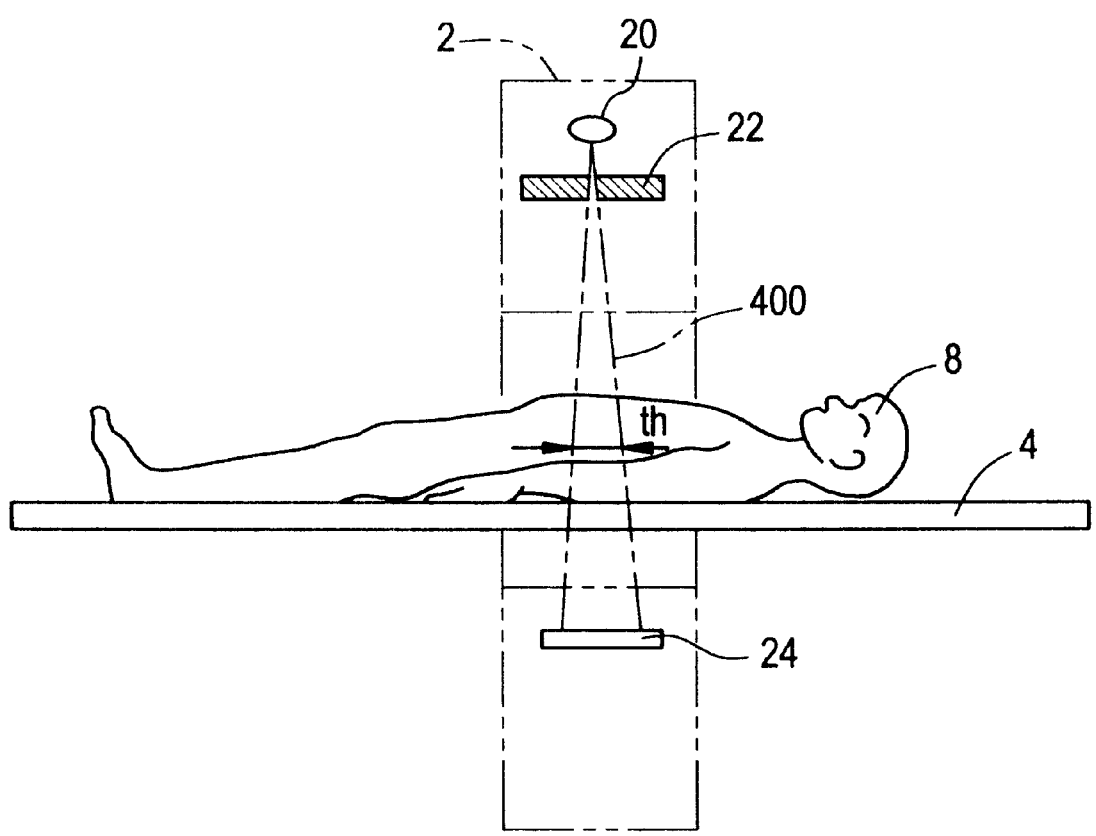

As exemplarily shown in FIG. 4, an object to be imaged 8 is rested on the imaging table 4, and is carried into the X-ray irradiation space with the object's body axis intersecting the fan surface of the X-ray beam 400. The scan gantry 2 has a cylindrical structure containing the X-ray emitting/detecting apparatus therein.

The X-ray irradiation space is formed in the internal space of the cylindrical structure of the scan gantry 2. An image of the object to be imaged 8 sliced by the X-ray beam 400 is projected on the detector array 24, and the detector array 24 detects the X-ray after passing through the object B. The slice thickness 'th' of the X-ray beam 400 impinging upon the object to be imaged 8 is regulated by the openness of an aperture of the collimator 22.

Figure 5:
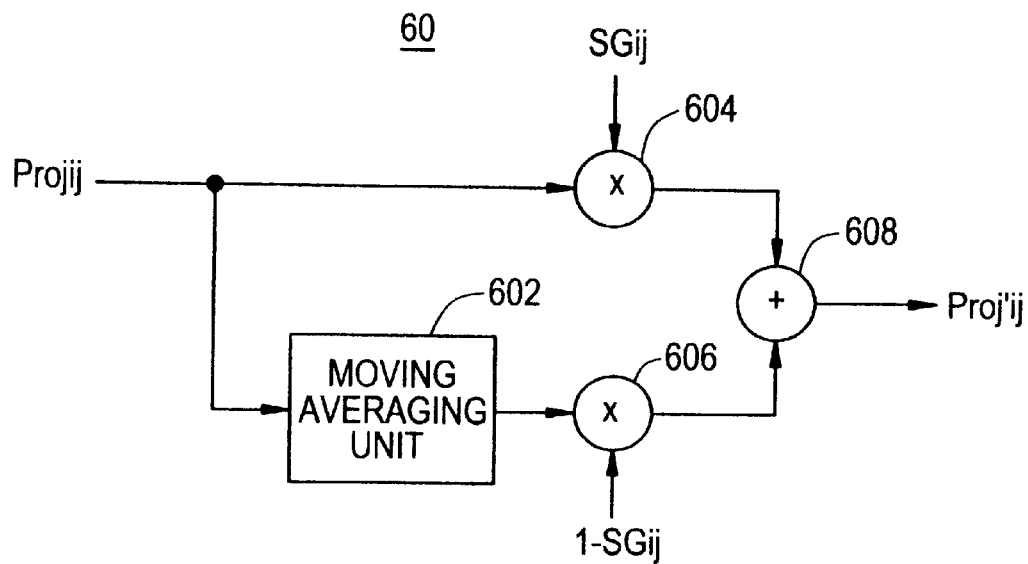
FIG. 5 is a block diagram of the central processing apparatus with respect to projection data correction function.

FIG. 5 shows a block diagram of the central processing apparatus 60 with respect to the projection data correction. The respective function of each block shown in FIG. 5 is implemented by, for example, a computer program. The central processing apparatus 60 shown in FIG. 5 is an embodiment of the projection data correction apparatus of the present invention. The configuration of the apparatus represents an embodiment of the apparatus in accordance with the present invention, and the operation of the apparatus represents an embodiment of the method in accordance with the present invention.

Figure 6:
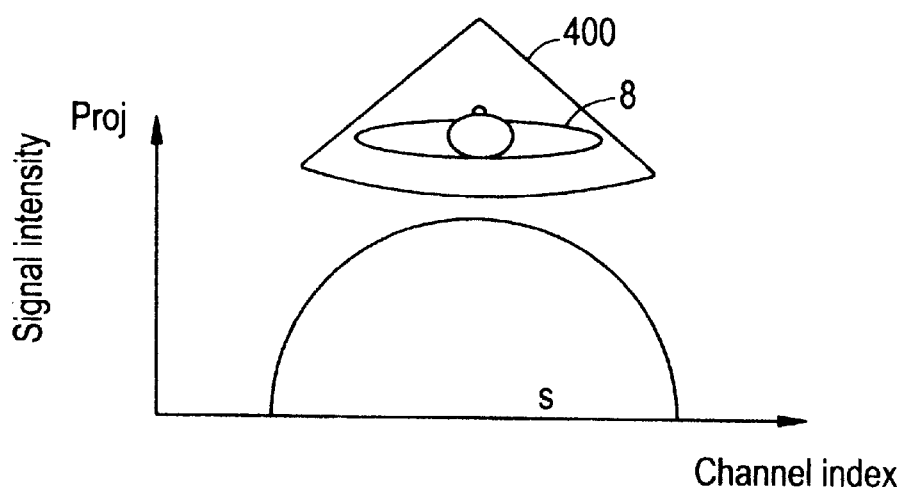
FIG. 6 illustrates 2 concept of a projection of an object to be imaged.

As shown, the central processing apparatus 60 has a moving averaging unit 602, which is an embodiment of the average value calculating means of the present invention. The moving average unit 602 individually calculates a moving average value in the direction of the channel 'i' for the projection data Proj__ij (wherein 'i'=channel index and 'j'=view index) constituting a projection of the object to be imaged 6 as exemplarily shown in FIG. 6. Data for use in the moving averaging are of proximate seven channels, for example.

The projection data Proj__ij is multiplied by a first weighting factor SGij at a multiplier 604. The multiplier 604 is an embodiment of the first product calculating means of the present invention. The first weighting factor SGij is given by the following equation;

$$SGij = 1 - \exp\{-Cij/\alpha\}, \quad (1)$$

wherein Cij is a count of the penetrating X-ray from which the projection data Proj__ij is derived. α is a function of the area of the projection 's', which is given by the following equation:

$$\alpha = f(s). \quad (2)$$

Particularly, α can be obtained by, for example, the following equation:

$$\alpha = A/s, \quad (2')$$

wherein A is an appropriate coefficient.

It should be noted that the correspondence between the area of the projection 's' and the constant α may be tabulated beforehand.

Figure 7:
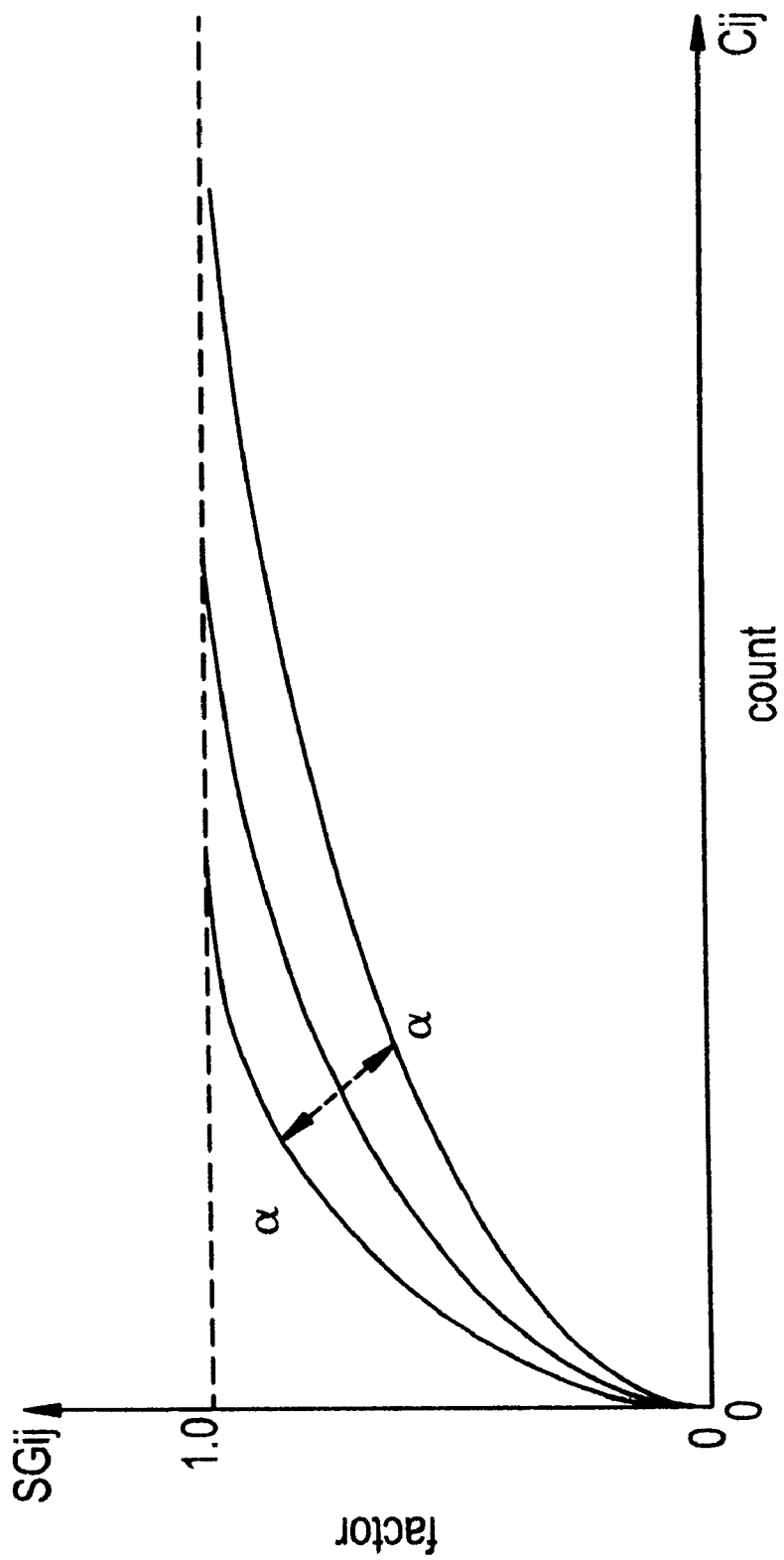
FIG. 7 Is a graphical representation illustrating a relationship between a count of a penetrating X-ray and a weighting factor.

A relationship between the count Cij and the factor SGij by Eq. (1) is graphically shown in FIG. 7.

A certain range having a small count Cij gives a first weighting factor SGij that is approximately proportional to Cij. Moreover, a is set as a function of the area of the projection 's', and is varied with the area of the projection.

Thus, a first weighting factor SGij can be obtained which is adapted for the cross-sectional area of the object to be imaged.

The moving average value of the projection data Proj_ij is multiplied by a second weighting factor (1−SGij) at a multiplier 606. The multiplier 606 is an embodiment of the second product calculating means of the present invention.

An adder 608 calculates the sum of output data from the multipliers 604 and 68. The adder 608 is an embodiment of the adder means of the present invention.

As a whole, the apparatus shown in FIG. 5 performs a calculation as follows:

$$Proj'ij = SGij \cdot Proj\_ij + (1-SGij)ave7\{Proj\_ij\}, \qquad (3)$$

wherein $$ave7\{Proj\_ij\}$$

represents moving averaging of date of seven channels proximate to the projection data Proj_ij.

Equation (3) can be rewritten as follows:

$$Proj'ij = ave7\{Proj\_ij\} + SGij(Proj\_ij - ave7\{Proj\_ij\}). \qquad (4)$$

A block diagram of an apparatus for performing the calculation given by Eq. (4) is shown in FIG. 8.

Figure 8:
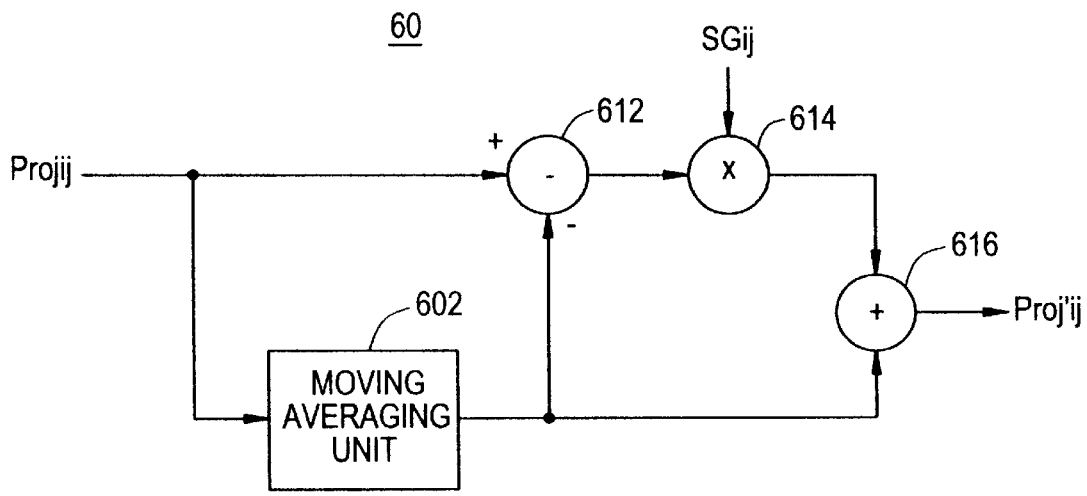
FIG. 8 is a block diagram of the central processing apparatus with respect to the projection data correction function.

In FIG. 8, components similar to those shown in FIG. 5 are denoted by similar symbols and description thereof will be omitted hereinafter.

A subtracter 612 calculates the difference between the projection data Proj_ij and its moving average value ave7{Proj_ij}. The difference is multiplied by the first weighting factor SGij at a multiplier 614. An adder 618 calculates the sum of output data from the multiplier 614 and output data from the moving averaging unit 602, i.e., the moving average value ave7 {Proj_ij}.

Both of Equations (3) and (4) indicate that a weighted addition is individually performed on the projection data and a moving average value containing the proximate data. The weight of the projection data in the result of the addition is decreased as the count of the penetrating X-ray from which the projection data 16 derived becomes smaller.

On the contrary, the weight of the moving average. value is complimentarily increased. Therefore, the weight of the moving average value is increased as the count becomes smaller. Thus, although projection data based on a small count has a poor SNR, the reduction in SNR can be compensated for by increasing the weight of the moving average value for that projection data as above.

Figure 9:
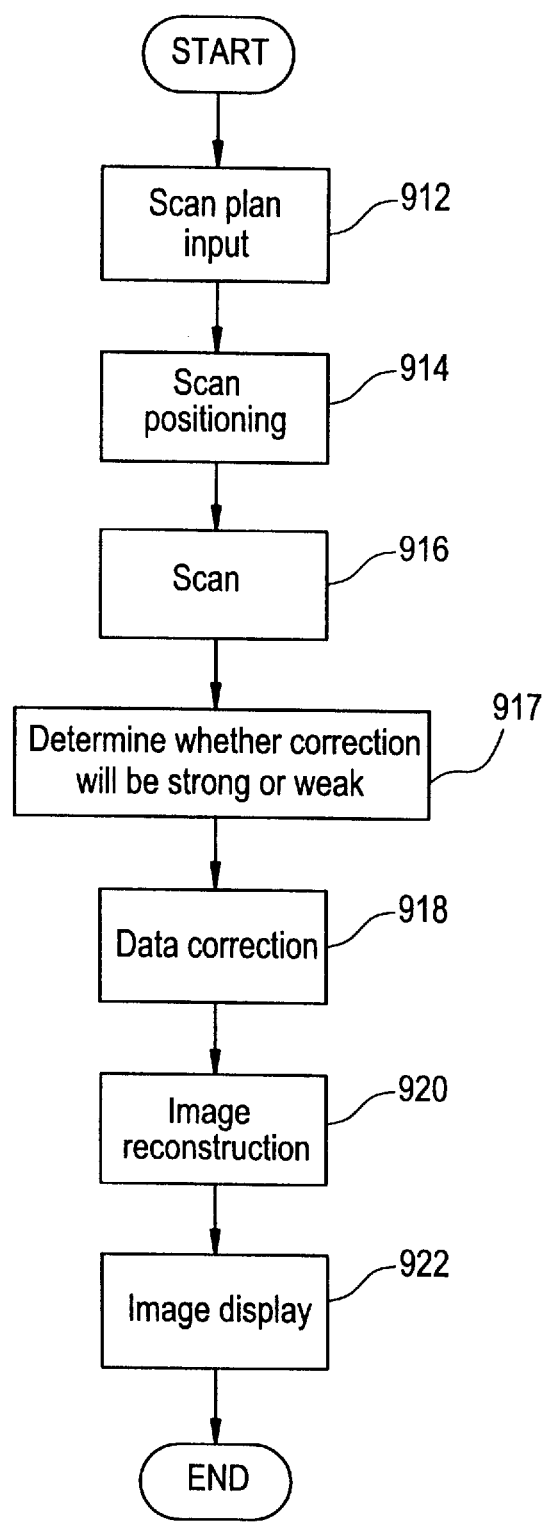

Now the operation of the present apparatus will be described. FIG. 9 shows a flow chart of the operation of the present apparatus As shown, a human operator inputs a scan plan via the operating device 70 at Step 912. The scan plan includes the condition under which the X-ray is emitted, slice thickness, slice position and so forth. Thereafter, the present apparatus operates under control of the operation by the human operator and the central processing apparatus 60 following the input scan plan.

At Step 914, scan positioning is performed. Specifically, the operator manipulates the operating device 70 to move the imaging table 4 and align the center of a site to be imaged of the object 8 with the center of rotation (i.e., isocenter) of the X-ray emitting/detecting apparatus.

At Step 916, a scan is performed. Specifically, the X-ray emitting/detecting apparatus is rotated around the object to be imaged 8 and collects projections for, for example, 1,000 views per rotation, into the data acquisition buffer 64.

At Step 917, the strength of the correction is determined depending upon the size of the object to be imaged so that a strong correction is applied when the size of the object to be imaged is small, and a weak correction is applied when the size of the object to be imaged is large.

Particularly, the constant a is calculated by Eq. (2) or (2') from the area of the projection 's' of a start view of a scan (or of data of a scout scan), or the constant $\alpha$ is found from a table in which the correspondence between the area of the projection 's' and the constant a is defined, When the area of the projection 's' is small, the constant $\alpha$ becomes large, hence a strong correction is applied. On the other hand, when the area of the projection 's' is large, the constant $\alpha$ becomes small, hence a week correction is applied.

At Steps 918 and 920, data correction and image reconstruction are respectively performed after or along with the scan.

Figure 10:
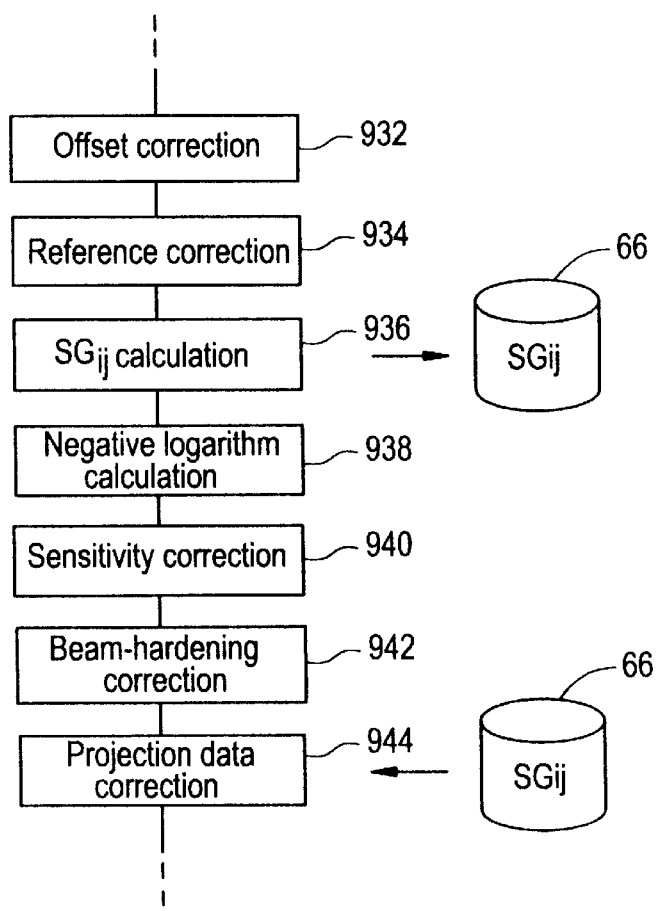
FIGS. 9 and 10 are flow charts of the operation of the apparatus shown in FIG. 1.

A detailed flow chart of the data correction at Step 918 is shown in FIG. 10. As shown, an offset correction is performed on the scan data at Step 932 for correcting an offset appended to the count of the penetrating X-ray.

Next, a reference correction is made at Step 934 for correcting the X-ray intensity by dividing the count of the penetrating X-ray by a count of the X-ray measured at a reference channel.

Then, at Step 936, a first weighting factor SGij is calculated. The first weighting factor SGij is calculated by Eq. (1) using the offset-corrected and reference-corrected count Cij, and is saved in the storage device 66.

Next, at Step 938, a negative logarithm of the count Cij is calculated.

Next, at Step 940, a sensitivity correction is performed.

Then, at Step 942, a beam-hardening correction is performed to generate projection data Proj_ij.

At Step 944, the projection data correction by Eq. (3) or (4) is performed on the projection data Proj_ij. The first weighting factor SGij for the correction calculation is read from the storage device 66 for use.

Returning to FIG. 9, the image reconstruction at Step 920 is performed by, for example, a filtered back projection technique using projections for a plurality of views comprised of data thus corrected.

At Step 922, the reconstructed tomographic image is displayed on the display device 68. The display image is a tomographic image with good quality not containing streaking artifacts or the like. Specifically, since the projection data correction at Step 944 in FIG. 10 compensates for SNR reduction in a portion having a low count, a directional noise pattern will not occur even when the thorax or abdomen is imaged with both the arms put on the sides of the body, for example, thereby preventing false images such as streaking artifacts from being contained in the reconstructed image.

While the preceding description is made on a case in which an X-ray is employed as radiation, the radiation is not limited to the X-ray but may be other types of radiation such as a γ-ray, However, the X-ray is preferred at the present time insofar as practical means for generation, detection, control and so forth of the X-ray are most well-improved.

Many widely different embodiments of the invention may be configured without departing from the spirit and the scope of the present invention. It should be understood that the present invention is not limited to the specific embodiments described in the specification, except as defined in the appended claims.

What is claimed is:

1. A projection data correction method comprising the steps of:

individually calculating an average value of data and its proximate data, said data constituting a projection of an object to be imaged by penetrating radiation;

calculating a first product by multiplying said data by a first weighting factor that corresponds to a count of the penetrating radiation from which said data is derived;

calculating a second product by multiplying said average value by a second weighting factor that is a complement of said first weighting factor with respect to one; and adding said first and second products, wherein said first weighting factor decreases as the corresponding count becomes smaller.

2. The method of claim 1, comprising the step of employing data obtained by a scout scan or data of a view of an axial scan to determine a rate at which the first weighting factor decreases as the corresponding count becomes smaller.

3. The method of claim 1, wherein said first weighting factor is given by the following equation:

$$1-e^{(-C/\alpha)},$$

wherein C is a count of the penetrating radiation from which said data is derived, and $\alpha$ is a constant determined by the area of said projection.

4. The method of claim 1, wherein said first weighting factor is approximately proportional to said count of said penetrating radiation.

5. The method of claim 1, further comprising the steps of:

emitting radiation toward an object to be imaged in a plurality of view directions;

detecting penetrating radiation; and producing an image using a projection based on signals detected by said emitting radiation and detection penetrating radiation.

6. The method of claim 5, wherein an X-ray is employed as said radiation.

7. The method of claim 5, wherein said first weighting factor is approximately proportional to said count of said penetrating radiation.

8. The method of claim 5, wherein said first weighting factor is given by the following equation:

$$1-e^{(-C/\alpha)},$$

wherein C is a count of the penetrating radiation from wheich said data is derived, and $\alpha$ is a constant determined by the area of said projection.

9. A projection data correction apparatus comprising:

average value calculating means for individually calculating an average value of data and its proximate data, said data constituting a projection of an object to be imaged by penetrating radiation;

first product calculating means for calculating a first product by multiplying said data by a first weighting factor that corresponds to a count of the penetrating radiation from which said data is derived;

second product calculating means for calculating a second product by multiplying said average value by a second weighting factor that is a complement of said first weighting factor with respect to one;

adder means for adding said first and second products; and first weighting factor determining means for determining said first weighting factor so that said first weighting factor decreases as the corresponding count becomes smaller.

10. The apparatus of claim 9, wherein said first weighting factor determining means employs data obtained by a scout scan or data of a view of an axial scan to determine a rate at which the first weighting factor is decreased as the corresponding count becomes smaller.

11. The apparatus of claim 9, wherein said first product calculating means uses said first weighting factor that is approximately proportional to said count of the penetrating radiation.

12. The apparatus of claim 9, wherein said first weighting factor is given by the following equation:

$$1-e^{(-C/\alpha)},$$

wherein C is a count of the penetrating radiation from which said data is derived, and $\alpha$ is a constant determined by the area of said projection.

13. The apparatus of claim 9, wherein an X-ray is employed as said radiation.

14. A radiation tomographic imaging apparatus comprising:

a radiation emitting/detecting means for emitting radiation toward an object to be imaged in a plurality of view directions and detecting penetrating radiation; and image producing means for producing an image using a projection based on signals detected by said radiation emitting/detecting means, wherein said image producing means comprises:

average value calculating means for individually calculating an average value of data and its proximate data, said data constituting said projection;

first product calculating means for calculating a first product by multiplying said data by a first weighting factor that corresponds to a count of the penetrating radiation from which said data is derived;

second product calculating means for calculating a second product by multiplying said average value by a second weighting factor that is a complement of said first weighting factor with respect to one;

adder means for adding said first and second products;

image reconstruction means for reconstructing an image using a projection comprised of data resulting from said addition; and first weighting factor determining means for determining said first weighting factor so that said first weighting factor decreases as the corresponding count becomes smaller.

15. The apparatus of claim 14, wherein said first weighting factor determining means employs data obtained by a scout scan or data of a view of an axial scan to determine a rate at which the first weighting factor is decreased as the corresponding count becomes smaller.

16. The apparatus of claim 14, wherein an X-ray is employed as said radiation.

17. The apparatus of claim 14, wherein said first product calculating means utilizes said first weighting factor that is approximately proportional to said count of said penetrating radiation.

18. The apparatus of claim 14, wherein said first weighting factor is given by the following equation:

$$1-e^{(-C/\alpha)},$$

wherein C is a count of the penetrating radiation from which said data is derived, and $\alpha$ is a constant determined by the area of said projection.

* * * * *